United States Patent [19]
O'Lenick, Jr.

[11] Patent Number: 5,274,101
[45] Date of Patent: Dec. 28, 1993

[54] POLYMERIC PHOSPHOLIPID POLYMERS

[75] Inventor: Anthony J. O'Lenick, Jr., Lilburn, Ga.

[73] Assignee: Siltech Inc., Norcross, Ga.

[21] Appl. No.: 1,672

[22] Filed: Jan. 7, 1993

[51] Int. Cl.$^5$ .................. C07F 9/6506; C07F 9/09
[52] U.S. Cl. .................. 548/112; 558/158; 558/159
[58] Field of Search .................. 558/158, 159; 548/112

[56] References Cited

U.S. PATENT DOCUMENTS

| | | |
|---|---|---|
| 4,209,449 | 6/1980 | Mayhew et al. |
| 4,215,064 | 7/1980 | Lindemann |
| 4,283,542 | 8/1981 | O'Lenick |
| 4,416,830 | 11/1983 | Morr et al. .................. 558/158 X |
| 4,503,002 | 3/1985 | Mayhew |

FOREIGN PATENT DOCUMENTS 0514588 11/1992 European Pat. Off. ............ 558/158

Primary Examiner—Mary C. Lee
Assistant Examiner—Michael G. Ambrose

[57] ABSTRACT

The present invention relates to a series of novel phospholipid polymers and processes for their use in personal care applications. The compounds of the present invention are prepared by the reaction of a suitable phosphating agent with a pendant hydroxyl group which is present on a polyoxyalkylene polymer, followed by neutralization to a pH of between 6 and 11, followed by the reaction with epichlorohydrin followed lastly by the reaction with a tertiary amine to give a quaternary compound.

9 Claims, No Drawings

POLYMERIC PHOSPHOLIPID POLYMERS

BACKGROUND OF THE INVENTION (1) Field of Invention

The present invention relates to a series of novel phospholipid polymers and processes for their use in personal care applications. The polymers by virtue of the presence of a mixed polyoxyethylene/polyoxypropylene glycol in correct location within in the molecule, and the polymeric nature of the compounds, result in liquidity, high foam, solubility and enhanced reactivity as well as inverse cloud point and film forming properties. The correct selection of the proper molecule results in the optimum combination of desired properties.

Since the compounds of the present invention are high molecular weight, they have a high degree of oxidative stability, even at elevated temperatures. In addition, these compounds are non volatile and unlike many other traditional fatty quaternary compounds are non yellowing when applied to textile substrates and are non irritating to eyes and skin.

The compounds of the present invention are prepared by the reaction of a suitable phosphating agent with a pendant hydroxyl group which is present on a polyoxyalkylene polymer, followed by neutralization to a pH of between 6 and 11, followed by the reaction with epichlorohydrin followed lastly by the reaction with a tertiary amine to give a quaternary compound. In a preferred embodiment the polyoxyalkylene glycol has been prepared by the reaction of both ethylene oxide and propylene oxide. In a more preferred embodiment, the ethylene oxide is at the terminal portion of the molecule and the propylene oxide is in the center. This results in the best combination of solubility and highest percentage reacted.

(2) Description of Arts and Practices

Fatty Phosphobetaines have been known since 1974. There are several patents which have issued on this topic.

U.S. Pat. No. 3,856,893 and 3,928,509 both issued to Diery disclose the basic technology used to make phosphobetaines and the alkyl derivatives.

Later, phosphobetaines based upon alkylamidoamines and imidazolines rather than alkyl amines were patented in U.S. Pat. No. 4,209,449 issued in 1980 to Mayhew and O'Lenick. This patent teaches that phosphate quats can be prepared by the reaction of a phosphate salt, three equivalents of epichlorohydrin and in a subsequent step, three equivalents of a tertiary amine.

U.S. Pat. No. 4,215,064 issued in 1980 to Lindemann et al teaches the basic technology that is used for the preparation of amido and imidazoline based phosphobetaines. These compounds can be prepared by the reaction of a phosphate salt, one equivalent of epichlorohydrin and one equivalent of a tertiary amine.

U.S. Pat. No. 4,243,602 issued in 1981 to O'Lenick and Mayhew teaches the basic technology that is used for the preparation of phosphobetaines based upon phosphorous acid salts. These compounds can be prepared by the reaction of a phosphorous acid salt, one equivalent of epichlorohydrin and one equivalent of a tertiary amine.

U.S. Pat. No. 4,261,911 issued in 1981 to Lindemann et al teaches the utilization of phosphobetaines based upon phosphorous acid. These compounds are useful as surfactants.

U.S. Pat. No. 4,283,542 issued in 1981 to O'Lenick and Mayhew teaches the process technology used for the preparation of phosphobetaines. These compounds can be prepared by the reaction of a phosphate salt, one equivalent of epichlorohydrin and one equivalent of a tertiary amine.

U.S. Pat. No. 4,336,386 issued in 1982 to O'Lenick and Mayhew teaches the technology for the preparation of imidazoline derived phosphobetaines based upon phosphorous acid salts. These compounds can be prepared by the reaction of a phosphorous acid salt, one equivalent of epichlorohydrin and one equivalent of an imidazoline.

U.S. Pat. No. 4,503,002 which is related to U.S. Pat. No. 4,209,449 issued in 1985 to Mayhew and O'Lenick teach that phosphate quats can be prepared by the reaction of a phosphate salt, three equivalents of epichlorohydrin and three equivalents of a tertiary amine.

U.S. Pat. No. 5,070,171 issued to O'Lenick teaches that silicone phosphate esters can be prepared by phosphating internal (i.e. non-terminal) dimethicone copolyols. U.S. Pat. No. 5,091,493 issued to O'Lenick teaches that non-polymeric silicone phosphobetaines can be prepared using the phosphate esters of U.S. Pat. No. 5,070,171.

It is also known that under certain catalytic conditions, epichlorohydrin reacts with certain alcohols to give an intermediate which can be used to react with tertiary amines to quaternary compounds. U.S. Pat. No. 3,445,440 to Susi (May 1969) and U.S. Pat. No. 3,517,045 to Susi (June 1970) teaches the use of chlorohydroxypropyl ether to alkylate specific tertiary amines which are the reaction product of a primary fatty amine and ethylene or propylene oxide. The compounds are used as antistatic agents in polymeric compositions such as polyolefin. The antistatic properties of these compounds are achieved by the minimization of static charges on the polymer surface. These anti-static materials are incorporated into the polymer melt and are effective by virtue of their insolubility in the molten polymer. The quaternary compounds migrate to the polymer surface and are effective antistatic agents.

U.S. Pat. No. 4,144,122 to Emanuelsson issued Mar. 13, 1979 teaches that tallow alcohol and certain other higher molecular weight alcohols and their alkoxylates can be reacted with epichlorohydrin, then subsequently with tertiary amines to give compounds suitable for paper debonding.

U.S. Pat. No. 4,215,064 to Lindemann et al issued Jul. 29, 1980 teaches that phosphobetaines can be prepared by the reaction of a phosphate or phosphite salt with epichlorohydrin under aqueous conditions. U.S. Pat. No. 4,283,541 to O'Lenick, et al, issued Aug. 11, 1981 teaches the process for the preparation of the phosphobetaines described in Lindemann (U.S. Pat. No. 4,215,064). None of these patents teach the compounds of the present invention. U.S. Pat. No. 4,800,077 issued January 1989 to O'Lenick teaches guerbet alcohol quaternary compounds can be prepared by reacting epichlorohydrin with guerbet alcohols then subsequently reacting the intermediate with amines.

SUMMARY OF THE INVENTION

The present invention relates to a series of novel polyoxyalkylene based phospholipid polymers. These compounds have phosphate functional groups connected via a hydroxypropyl group to a amine group. The amine group typically will be a quaternized nitrogen. Hence the products are amphoterics having both an anionic and cationic group present on the same pendant group. The polymer by virtue of this unique pendent group is highly foaming, non irritating to eyes and skin and deposits on fiber surfaces and form effective surface modifying finishes. The compounds of the present invention are therefore very well suited to applications in the personal care market.

The compounds of the present invention are prepared by the phosphation of polyoxyalkylene glycol, followed by reaction with epichlorohydrin (one or two mole equivalents) followed by reaction with amines. These amines can be primary secondary or tertiary.

Polyoxyalkylene glycols are commercially available from many sources and conform to the following structure:

H—O—[—CH$_2$—CH$_2$—O]$_a$—[—CH$_2$—CH(CH$_3$)—O]$_b$—[—CH$_2$—CH$_2$—O]$_c$—CH$_2$—CH(CH$_3$)—O]$_d$—H

One of the reasons why the product produced by the process of the present invention is that the polyoxyalkylene glycol has two terminal reactive groups. The phosphation reaction of the two groups gives mono and di phosphate ester. The di phosphate ester is a crosslinking group between polyoxyalkylene glycols forming both monoester and diester at each of the two hydroxyl groups.

HO-"polyoxyalkylene"-OH + Phosphating agent ⟶

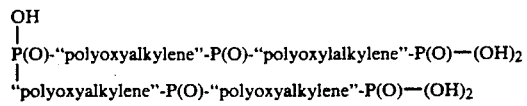

wherein "polyoxyalkylene" is

—O—[—CH$_2$—CH$_2$—O]$_a$—[—CH$_2$—CH(CH$_3$)—O]$_b$—[—CH$_2$—CH$_2$—O]$_c$[—CH$_2$—CH(CH$_3$)—O]$_d$—

A second reason for the extended polymeric nature of the products of the present invention occurs as a consequence of the reaction with epichlorohydrin;

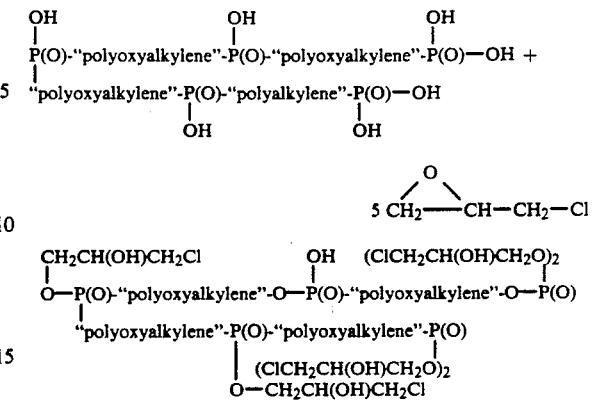

By reacting less on a molar basis of epichlorohydrin less of the phosphate groups are derivatized and the polymer's molecular weight is decreased.

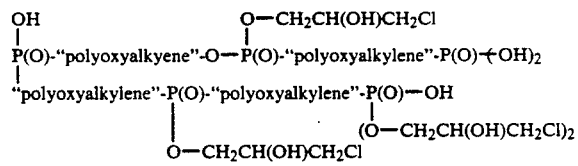

Thereby the polymeric structure can be regulated.

Finally, the intermediate is reacted with an amine to give a phospholipid polymer.

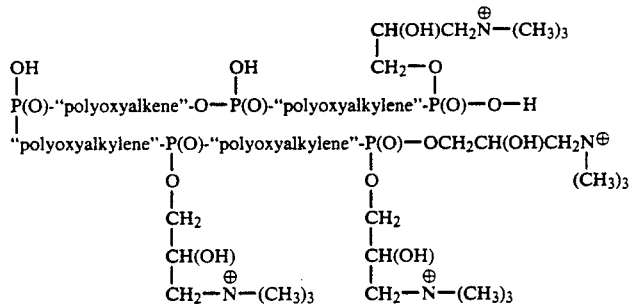

The compounds of the present invention unlike many other surface active agents which form micelles, unexpectedly form bilayers in aqueous solution by orientating themselves into the lowest energy configuration which happens to be sheets.

The compounds of this invention are prepared by the reaction of (a) a polyoxyalkylene glycol conforming to the following structure;

H—O—[—CH$_2$—CH$_2$—O]$_a$—[—CH$_2$—CH(CH$_3$)—O]$_b$—[—CH$_2$—CH$_2$—O]$_c$[—CH$_2$—CH(CH$_3$)—O]$_d$—H wherein a, b and c are independently integers each raging from 0 to 200 with the proviso that the sum of a+b+c range from 1 to 400; with (b) a phosphating agent selected from the group consisting of polyphosphoric acid, phosphoric anhydride and phosphorus oxychloride said reaction to be conducted at a temperature of between 30 and 80 C.;

followed by
- (c) neutralization of the phosphate with a base selected from the group consisting of NaOH, KOH, NH4OH, LiOH, in aqueous solution having a solid content of between 20 and 70% by weight to a pH of between 5 and 11;

followed by
- (d) the condensation reaction with epichlorohydrin at a temperature of between 80 and 100 C. for four to ten hours and subsequently;
- (e) conducting an n-alkylation reaction with an amine selected from the group consisting of

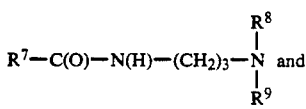

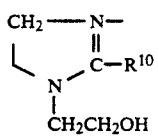

$R^4$ is alkyl having from 1 to 20 carbon atoms;
$R^5$ is alkyl having from 1 to 20 carbon atoms;
$R^6$ is alkyl having from 1 to 20 carbon atoms;
$R^7$ is alkyl having from 1 to 20 carbon atoms;
$R^8$ and $R^9$ are independently selected from lower alkyl having from one to three carbon atoms;
$R^{10}$ is alkyl having from 6 to 20 carbon atoms;
said n-alkylation reaction conducted at a temperature of between 50 and 100 C.

RAW MATERIAL EXAMPLE

Polyoxyalkylene Glycol Compounds

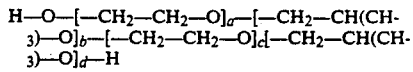

wherein; a, b and c are independently integers each raging from 0 to 200 with the proviso that the sum of a+b+c range from 1 to 400

Class 1: Polyoxyethylene Glycols (b, c, and d are all 0.)

The following examples are presented with the values of a and as determined by analysis. Since products covered by trade name can change, the structure rather than the trade name is considered more important as an example.

| Example | Trade Name | Molecular Weight | a |
|---|---|---|---|
| 1 | Phenoxide E-400 | 200 | 4 |
| 2 | Phenoxide E-300 | 300 | 6 |
| 3 | Phenoxide E-400 | 400 | 8 |
| 4 | Phenoxide E-600 | 600 | 12 |
| 5 | Phenoxide E-900 | 900 | 20 |
| 6 | Phenoxide E-1000 | 1,000 | 22 |
| 7 | Phenoxide E-1450 | 1,450 | 32 |
| 8 | Phenoxide E-3350 | 3,350 | 74 |
| 9 | Phenoxide E-4600 | 4,600 | 104 |
| 10 | Phenoxide E-8000 | 8,000 | 180 |

Phenoxide is a registered trademark of Phoenix Chemical Inc.

Class 2

H—O—[—CH2—CH2—O]a—[—CH2—CH(CH3)—O]b—[—CH2—CH2—O]c[—CH2—CH(CH3)—O]d—H

The following examples are presented with the values of a, b and c as determined by analysis. Since products covered by trade name can change, the structure, rather than the trade name is considered more important as an example.

| Example | Trade Name | a | b | c |
|---|---|---|---|---|
| 11 | Phoenix L-31 | 1.0 | 2.1 | 1.0 |
| 12 | Phoenix L-35 | 5.0 | 10.0 | 5.0 |
| 13 | Phoenix L-42 | 2.5 | 5.0 | 2.5 |
| 14 | Phoenix L-43 | 3.0 | 8.0 | 3.0 |
| 15 | Phoenix L-44 | 6.0 | 11.0 | 6.0 |
| 16 | Phoenix L-61 | 2.0 | 4.0 | 2.0 |
| 17 | Phoenix L-62 | 4.0 | 8.0 | 4.0 |
| 18 | Phoenix L-63 | 6.0 | 12.0 | 6.0 |
| 19 | Phoenix L-64 | 8.0 | 16.0 | 8.0 |
| 20 | Phoenix L-72 | 5.0 | 9.5 | 5.0 |
| 21 | Phoenix L-81 | 3.0 | 5.0 | 3.0 |
| 22 | Phoenix L-92 | 6.0 | 12.5 | 6.0 |
| 23 | Phoenix L-101 | 4.0 | 7.5 | 4.0 |
| 24 | Phoenix L-121 | 4.5 | 9.0 | 4.5 |
| 25 | Phoenix L-122 | 9.0 | 18.0 | 9.0 |

Phoenix is a registered trademark of Phoenix Chemical

Class 3: Polyoxypropylene Compounds (a, c and d are each 0)

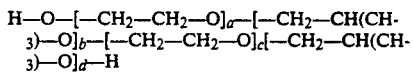

a, c and d are all zero.

| Example | Trade Name | Molecular Weight | b |
|---|---|---|---|
| 26 | Alkapol PPG 425 | 425 | 7 |
| 27 | Alkapol PPG 600 | 600 | 10 |
| 28 | Alkapol PPG 1000 | 1000 | 17 |

Alkapol is a registered trade mark of Alkaril Chemicals Inc. Winder Ga.

Class 4

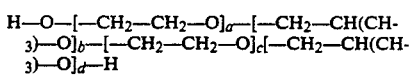

The following examples are presented with the values of b, c and d as determined by analysis.

| Example | Trade Name | b | c | d |
|---|---|---|---|---|
| 29 | Phoenix R 4 | 1.0 | 2.1 | 1.0 |
| 30 | Phoenix R 20 | 5.0 | 10.0 | 5.0 |
| 31 | Phoenix R 10 | 2.5 | 5.0 | 2.5 |
| 32 | Phoenix R 16 | 4.0 | 8.0 | 4.0 |
| 33 | Phoenix R 22 | 6.0 | 11.0 | 6.0 |
| 34 | Phoenix R 8 | 2.0 | 4.0 | 2.0 |
| 35 | Phoenix R 14 | 3.0 | 8.0 | 3.0 |
| 36 | Phoenix R 2 | 6.0 | 12.0 | 6.0 |
| 37 | Phoenix R 32 | 8.0 | 16.0 | 8.0 |
| 38 | Phoenix R 19 | 5.0 | 9.0 | 5.0 |
| 39 | Phoenix R 11 | 3.0 | 5.0 | 3.0 |
| 40 | Phoenix R 24 | 6.0 | 12.5 | 6.0 |
| 41 | Phoenix R 15 | 4.0 | 7.5 | 4.0 |
| 42 | Phoenix R 18 | 4.5 | 9.0 | 4.5 |
| 43 | Phoenix R 36 | 9.0 | 18.0 | 9.0 |

| Example | Trade Name | b | c | d |
|---|---|---|---|---|
| 44 | Phoenix R 101 | 10.0 | 10.0 | 10.0 |

Preparation of the Polyoxyalkylene Glycol Phosphate

The following examples further illustrate the objects and advantages of this invention, though it should be understood that the various reactants and amounts thereof, reaction conditions, and other details are merely illustrative and should not be construed to unduly limit this invention.

EXAMPLE 45-68

The specified amount of polyoxyalkylene glycol (Examples 1-44) is added to a suitable reaction vessel. 56.5 grams of polyphosphoric acid is added to under good agitation over a 2 hr. period. The exothermic reaction raises the temperature of the mixture to about 70 C. After 1 hour slowly raise the temperature to 100 C. and hold 2-4 hours. The resulting material is diluted with water and the pH is adjusted to 9.0 with NaOH.

| Example | Polyoxyalkylene glycol Example Number | Grams |
|---|---|---|
| 45 | 1 | 100 |
| 46 | 2 | 150 |
| 47 | 3 | 200 |
| 48 | 4 | 300 |
| 49 | 5 | 450 |
| 50 | 6 | 500 |
| 51 | 7 | 725 |
| 52 | 8 | 1,675 |
| 53 | 9 | 2,300 |
| 54 | 10 | 4,000 |
| 55 | 11 | 900 |
| 56 | 12 | 106 |
| 57 | 13 | 515 |
| 58 | 14 | 258 |
| 59 | 14 | 368 |
| 60 | 15 | 589 |
| 61 | 16 | 206 |
| 62 | 17 | 412 |
| 63 | 18 | 618 |
| 64 | 19 | 824 |
| 65 | 20 | 501 |
| 66 | 21 | 280 |
| 67 | 22 | 632 |
| 68 | 23 | 441 |

EXAMPLE 69-88

The specified amount of polyoxyalkylene glycol (Examples 1-44) is added to a suitable reaction vessel. 36.5 grams of $P_2O_5$ is added to under good agitation over a 2 hr. period. The exothermic reaction raises the temperature of the mixture to about 70 C. After 1 hour slowly raise the temperature to 100 C and hold 2-4 hours. The resulting material is diluted with water and the pH is adjusted to 9.0 with KOH.

| Example | Polyoxyalkylene glycol Example Number | Grams |
|---|---|---|
| 69 | 24 | 463 |
| 70 | 25 | 927 |
| 71 | 26 | 213 |
| 72 | 27 | 300 |
| 73 | 28 | 500 |
| 74 | 29 | 105 |
| 75 | 30 | 515 |
| 76 | 31 | 258 |
| 77 | 32 | 412 |
| 78 | 33 | 596 |
| 79 | 34 | 206 |
| 80 | 35 | 353 |
| 81 | 36 | 618 |
| 82 | 37 | 824 |
| 83 | 38 | 493 |
| 84 | 39 | 287 |
| 85 | 40 | 629 |
| 86 | 41 | 401 |
| 87 | 42 | 463 |
| 88 | 43 | 927 |

Preparation of the Polyoxyalkylene glycol Phosphate-epichlorohydrin Adduct

The following examples further illustrate the objects and advantages of this invention, though it should be understood that the various reactants and amounts thereof, reaction conditions, and other details are merely illustrative and should not be construed to unduly limit this invention.

EXAMPLE 89-132

The polyoxyalkylene glycol phosphate (Examples 45-88) is added 50 grams of epichlorohydrin. The temperature is raised to between 70 C and 88 C. After 1 hour slowly raise the temperature to 100 C and hold 2-4 hours.

| Example | Polyoxyalkylene glycol Example Number | Grams |
|---|---|---|
| 89 | 45 | 100 |
| 90 | 46 | 150 |
| 91 | 47 | 200 |
| 92 | 48 | 300 |
| 93 | 49 | 450 |
| 94 | 50 | 500 |
| 95 | 51 | 725 |
| 96 | 52 | 1,675 |
| 97 | 53 | 2,300 |
| 98 | 55 | 4,000 |
| 99 | 56 | 900 |
| 100 | 57 | 106 |
| 101 | 58 | 515 |
| 102 | 59 | 258 |
| 103 | 60 | 368 |
| 104 | 61 | 589 |
| 105 | 62 | 206 |
| 106 | 63 | 412 |
| 107 | 64 | 618 |
| 108 | 65 | 824 |
| 109 | 66 | 501 |
| 110 | 67 | 280 |
| 111 | 68 | 632 |
| 112 | 69 | 441 |
| 113 | 70 | 463 |
| 114 | 71 | 927 |
| 115 | 72 | 213 |
| 116 | 73 | 300 |
| 117 | 74 | 500 |
| 118 | 75 | 105 |
| 119 | 76 | 515 |
| 120 | 77 | 258 |
| 121 | 78 | 412 |
| 122 | 79 | 596 |
| 123 | 80 | 206 |
| 124 | 81 | 353 |
| 125 | 82 | 618 |
| 126 | 83 | 824 |
| 127 | 84 | 493 |
| 128 | 85 | 287 |

-continued

| Example | Polyoxyalkylene glycol Example Number | Grams |
| --- | --- | --- |
| 129 | 86 | 629 |
| 130 | 87 | 401 |
| 131 | 88 | 463 |
| 132 | 89 | 927 |

QUATERNARY REACTION SEQUENCE

The following examples further illustrate the objects and advantages of this invention, though it should be understood that the various reactants and amounts thereof, reaction conditions, and other details are merely illustrative and should not be construed to unduly limit this invention.

AMINE REACTANT GROUP 1

The reactants are tertiary amines conforming to the following structure;

$$R^4-\underset{\underset{R^5}{|}}{\overset{\overset{R^6}{|}}{N}}-R^5$$

| Example Number | $R^4$ | $R^5$ | $R^6$ |
| --- | --- | --- | --- |
| 133 | $C_{10}H_{21}$ | $CH_3$ | $CH_3$ |
| 134 | $C_{12}H_{25}$ | $CH_3$ | $CH_3$ |
| 135 | $C_{14}H_{29}$ | $CH_3$ | $CH_3$ |
| 136 | $C_{16}H_{33}$ | $CH_3$ | $CH_3$ |
| 137 | $C_{18}H_{37}$ | $CH_3$ | $CH_3$ |
| 138 | $C_{20}H_{41}$ | $CH_3$ | $CH_3$ |
| 139 | $C_{10}H_{21}$ | $C_{16}H_{33}$ | $CH_3$ |
| 140 | $C_{12}H_{25}$ | $C_{18}H_{37}$ | $CH_3$ |
| 141 | $C_{14}H_{29}$ | $C_{20}H_{41}$ | $CH_3$ |
| 142 | $C_{16}H_{33}$ | $C_{10}H_{21}$ | $CH_3$ |
| 143 | $C_{18}H_{37}$ | $C_{12}H_{25}$ | $CH_3$ |
| 144 | $C_{20}H_{41}$ | $C_{14}H_{29}$ | $CH_3$ |
| 145 | $C_6H_{13}$ | $C_6H_{13}$ | $C_6H_{13}$ |
| 146 | $C_2H_5$ | $CH_3$ | $C_2H_5$ |
| 147 | $C_{10}H_{21}$ | $C_{10}H_{21}$ | $C_{10}H_{21}$ |

AMINE REACTANT GROUP 2

The reactants are amido-tertiary amines conforming to the following structure;

$$R^7-C(O)N(H)-CH_2)_3-\underset{\underset{R^9}{|}}{\overset{\overset{R^8}{|}}{N}}-R^9$$

| Example Number | $R^7$ | $R^8$ | $R^9$ |
| --- | --- | --- | --- |
| 148 | $C_5H_{11}$ | $CH_3$ | $CH_3$ |
| 149 | $C_7H_{15}$ | $CH_3$ | $CH_3$ |
| 150 | $C_9H_{19}$ | $CH_3$ | $CH_3$ |
| 151 | $C_{11}H_{23}$ | $CH_3$ | $CH_3$ |
| 152 | $C_{13}H_{27}$ | $CH_3$ | $CH_3$ |
| 153 | $C_{15}H_{31}$ | $CH_3$ | $CH_3$ |
| 154 | $C_{17}H_{35}$ | $CH_3$ | $CH_3$ |
| 155 | $C_{19}H_{39}$ | $CH_3$ | $CH_3$ |
| 156 | $C_{19}H_{39}$ | $CH_2CH_3$ | $CH_2CH_3$ |
| 157 | $C_{11}H_{23}$ | $CH_2CH_3$ | $CH_2CH_3$ |
| 158 | $C_5H_{11}$ | $CH_2CH_3$ | $CH_2CH_3$ |
| 159 | $C_5H_{11}$ | $CH_3$ | $CH_3$ |
| 160 | $C_7H_{15}$ | $CH_3$ | $CH_3$ |
| 161 | $C_9H_{19}$ | $CH_3$ | $CH_3$ |
| 162 | $C_{11}H_{23}$ | $CH_3$ | $CH_3$ |
| 163 | $C_{13}H_{27}$ | $CH_3$ | $CH_3$ |
| 164 | $C_{15}H_{31}$ | $CH_3$ | $CH_3$ |
| 165 | $C_{17}H_{35}$ | $CH_3$ | $CH_3$ |
| 166 | $C_{19}H_{39}$ | $CH_3$ | $CH_3$ |

AMINE REACTANT GROUP 3

The reactants are imidazoline compounds conforming to the following structure;

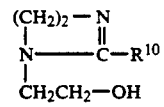

| Example Number | $R^{10}$ |
| --- | --- |
| 167 | $C_5H_{11}$ |
| 168 | $C_7H_{15}$ |
| 169 | $C_9H_{19}$ |
| 170 | $C_{11}H_{23}$ |
| 171 | $C_{13}H_{27}$ |
| 172 | $C_{15}H_{31}$ |
| 173 | $C_{17}H_{35}$ |
| 174 | $C_{19}H_{39}$ |

GENERAL REACTION PROCEDURE

To a suitable flask, containing the phosphate-epichlorohydrin adduct (Examples 89–132), heat to 50 C., is added the specified amount of the type of amine reactant under good agitation. The reaction mass is heated to 85–95 C. and held from between 5 and 15 hours. The reaction progress is monitored by % inorganic chloride, which approaches 98% of theoretical.

EXAMPLE 131

To a suitable flask, equipped with a thermometer and agitator containing the phosphate epichlorohydrin adduct example 89, is added add 52.0 grams of amine reactant (Example 89). Next add the specified amount of the specified halo intermediate (example 45) under good agitation. The reaction mass is heated to 85–95 C. and held from between 5 and 10 hours. The reaction progress is monitored by % inorganic chloride, which approaches 98% of theoretical.

EXAMPLES 132–175

Example 131 is repeated, only this time the specified amount of the specified intermediate is substituted.

| | Amine Reactants | | Phosphate-Epichlorohydrin Adduct | |
| --- | --- | --- | --- | --- |
| Example | Example | Grams | Example | Grams |
| 175 | 133 | 100.5 | 89 | 376.0 |
| 176 | 134 | 113.5 | 90 | 480.0 |
| 177 | 135 | 128.5 | 91 | 672.0 |
| 178 | 136 | 139.5 | 92 | 920.0 |
| 179 | 137 | 152.5 | 93 | 1080.0 |
| 180 | 138 | 182.0 | 94 | 1523.0 |
| 181 | 139 | 203.0 | 95 | 3400.0 |
| 182 | 140 | 229.0 | 96 | 4800.0 |
| 183 | 141 | 182.0 | 97 | 8080.0 |
| 184 | 142 | 203.0 | 98 | 200.0 |
| 185 | 143 | 229.0 | 99 | 600.0 |
| 186 | 144 | 125.5 | 100 | 400.0 |
| 187 | 145 | 35.0 | 101 | 450.0 |
| 188 | 146 | 218.5 | 102 | 675.0 |
| 189 | 147 | 99.5 | 103 | 290.0 |
| 190 | 148 | 113.5 | 104 | 490.0 |
| 191 | 149 | 127.5 | 104 | 700.0 |
| 192 | 150 | 141.5 | 106 | 900.0 |
| 193 | 151 | 155.5 | 107 | 600.0 |
| 194 | 152 | 169.5 | 108 | 400.0 |
| 194 | 153 | 183.5 | 109 | 705.0 |
| 196 | 154 | 197.5 | 110 | 325.0 |
| 197 | 155 | 168.5 | 111 | 710.0 |
| 198 | 156 | 155.5 | 112 | 1000.0 |

-continued

| Example | Amine Reactants Example | Grams | Phosphate-Epichloro-hydrin Adduct Example | Grams |
|---|---|---|---|---|
| 199 | 157 | 113.5 | 113 | 401.0 |
| 200 | 158 | 320.0 | 114 | 455.0 |
| 201 | 159 | 2464.0 | 115 | 605.0 |
| 202 | 160 | 150.0 | 116 | 180.0 |
| 203 | 161 | 164.0 | 117 | 600.0 |
| 204 | 162 | 891.0 | 118 | 350.0 |
| 205 | 163 | 685.0 | 119 | 506.0 |
| 206 | 164 | 551.5 | 120 | 725.0 |
| 207 | 165 | 565.5 | 121 | 300.0 |
| 208 | 166 | 92.0 | 122 | 425.0 |
| 209 | 167 | 106.0 | 123 | 700.0 |
| 210 | 168 | 120.0 | 124 | 900.0 |
| 211 | 169 | 134.0 | 125 | 600.0 |
| 212 | 170 | 148.0 | 126 | 400.0 |
| 213 | 171 | 162.0 | 127 | 700.0 |
| 214 | 172 | 176.0 | 128 | 500.0 |
| 215 | 173 | 176.0 | 129 | 600.0 |
| 216 | 173 | 175.0 | 130 | 1000.0 |
| 217 | 174 | 92.5 | 131 | 300.0 |

RESULTS

The compounds of the present invention were found to be non-irritating to the skin and eyes, and possess unique surface active properties. These include detergency and wetting properties. Surprisingly, these materials were also found to have a mitigating effect upon eye irritation of standard anionic materials like sodium lauryl sulfate and stearyl dimethyl benzalkonium chloride.

Compounds containing propylene oxide were found to be less soluble in water than the ethylene oxide containing compounds.

What is claimed:

1. A polymeric phospholipid prepared by the n-alkylation reaction of an intermediate conforming to the following structure;

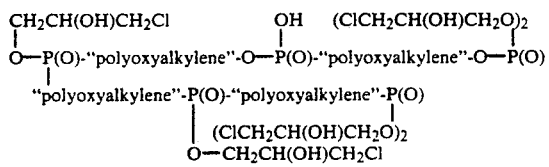

wherein "polyoxyalkylene" is

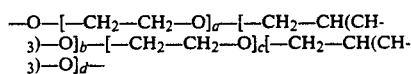

a, b and c are independently integers each ranging from 0 to 200 with the proviso that the sum of a+b+c range from 1 to 400;

d is an integer ranging from 0 to 10;

with an amine selected from the group consisting of;

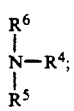

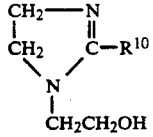

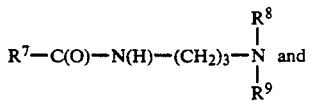

$R^4$ is alkyl having from 1 to 20 carbon atoms;
$R^5$ is alkyl having from 1 to 20 carbon atoms;
$R^6$ is alkyl having from 1 to 20 carbon atoms;
$R^7$ is alkyl having from 1 to 20 carbon atoms;
$R^8$ and $R^9$ are independently selected from lower alkyl having from one to three carbon atoms;
$R^{10}$ is alkyl having from 6 to 20 carbon atoms.

2. A polymeric phospholipid of claim 1 wherein said amine conforms to the following structure;

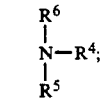

$R^4$ is alkyl having from 1 to 20 carbon atoms;
$R^5$ is alkyl having from 1 to 20 carbon atoms;
$R^6$ is alkyl having from 1 to 20 carbon atoms.

3. A polymeric phospholipid of claim 1 wherein said amine conforms to the following structure;

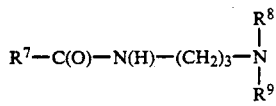

$R^7$ is alkyl having from 1 to 20 carbon atoms;
$R^8$ and $R^9$ are independently selected from lower alkyl having from one to three carbon atoms.

4. A polymeric phospholipid of claim 1 wherein said amine conforms to the following structure;

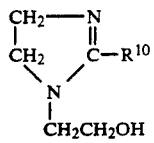

$R^{10}$ is alkyl having from 6 to 20 carbon atoms.

5. A polymeric phospholipid of claim 4 wherein $R^{10}$ is alkyl having 12 carbon atoms.

6. A polymeric phospholipid of claim 4 wherein $R^{10}$ is alkyl having 12 carbon atoms.

7. A polymeric phospholipid of claim 3 wherein $R^7$ is alkyl having 10 carbon atoms.

8. A polymeric phospholipid of claim 3 wherein $R^7$ is alkyl having 12 carbon atoms.

9. A polymeric phospholipid of claim 2 wherein
$R^4$ is alkyl having from 1 carbon atom;
$R^5$ is alkyl having from 1 carbon atom;
$R^6$ is alkyl having 12 carbon atoms.

* * * * *